United States Patent [19]

Ichikawa et al.

[11] Patent Number: 5,726,217

[45] Date of Patent: Mar. 10, 1998

[54] TETRAPHENOL COMPOUNDS AND PROCESS FOR PRODUCING THE SAME

[75] Inventors: Koji Ichikawa; Haruyoshi Osaki, both of Osaka; Jun Tomioka, Hyogo, all of Japan

[73] Assignee: Sumitomo Chemical Company, Limited, Osaka, Japan

[21] Appl. No.: 613,243

[22] Filed: Mar. 8, 1996

[30] Foreign Application Priority Data

Mar. 8, 1995 [JP] Japan .................. 7-048219

[51] Int. Cl.⁶ ............... C08F 2/50; G03C 1/695; G07C 39/15; G07C 309/53
[52] U.S. Cl. .......... 522/59; 522/162; 430/270.1; 534/557
[58] Field of Search .............. 534/557; 522/59, 522/162; 430/270.1

[56] References Cited

U.S. PATENT DOCUMENTS 5,153,096  10/1992  Uenishi et al. ................. 430/192
5,384,228  1/1995  Uetani et al. .................. 430/192
5,407,779  4/1995  Uetani et al. .................. 430/192

FOREIGN PATENT DOCUMENTS 5204148  8/1993  Japan.

*Primary Examiner*—Susan W. Berman
*Attorney, Agent, or Firm*—Birch, Stewart, Kolasch & Birch, LLP

[57] ABSTRACT

A tetraphenol compound represented by the formula (I):

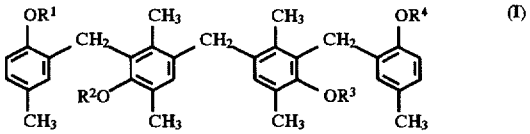

wherein $R^1$, $R^2$, $R^3$ and $R^4$ represent hydrogen 1,2-naphthoquinonediazide-4-sulfonyl or 1,2-naphthoquinonediazide-5-sulfonyl and a method for producing the compound are provided, and the compound can be used as a photosensitizer for a positive resist which exhibits superior properties.

8 Claims, No Drawings

TETRAPHENOL COMPOUNDS AND PROCESS FOR PRODUCING THE SAME

The present invention relates to novel tetraphenol compounds, a process for producing the same and their use for producing a photosensitizer.

It has been generally known that quinonediazide sulfonic acid esters of compounds having a phenolic hydroxyl group are used as photosensitizers in photosensitive resin compositions for minute processing in the production of semiconductors. These compositions are used as positive resists utilizing the fact that when a composition comprising a compound having a quinonediazide group and a novolak resin is applied on a substrate, which is then irradiated with a light of 300–500 nm, the quinonediazide group is decomposed to form a carboxyl group, allowing to change the composition from an alkali-insoluble state to an alkali-soluble state. Since such positive resists are characterized in that they are excellent in resolution as compared with negative resists, they have been used in producing various kinds of integrated circuits for semiconductors.

In recent years, the integrated circuits in the semi-conductor industries have gone on increasing minuteness with a rise in integration level of semi-conductor and now formation of a pattern in submicron order is demanded. Resolution in the lithographic process is very important in the production of integrated circuits and a more excellent resolution (high γ-value) is required for the positive resists.

Many kinds of quinonediazide compounds or novolak resins have been proposed as ingredients for positive resists. For example, JP-A-1-189644 (corr. to U.S. Pat. No. 5,153,096) has disclosed use of quinonediazide sulfonic acid esters of triphenylmethane compounds having at least two phenolic hydroxyl groups as photosensitizers. Even when these known sensitizers were used, however, improvement in the γ-value has not been satisfactory yet as the resist for current very minute process in the production of ultrahigh integrated circuits, so-called submicron lithography. Therefore, further improvements in properties as positive resist such as sensitivity, resolution and heat resistance are required.

An object of the present invention is to provide novel phenol compounds usable as photosensitive components for photosensitive resin compositions or usable as starting materials for producing such components.

Another object of the present invention is to provide photosensitive resin compositions which are well balanced among various properties as the resist such as high sensitivity, high resolution, high heat resistance, good profile, good focus allowance and little development residue using such compounds.

Inventors of the present invention have successfully produced phenol compounds of a specific structure having four phenolic hydroxyl groups, and have found that the above object can be attained by using quinonediazide esters of these compounds as the photosensitizers. Thus, the present invention have been completed.

The present invention provides tetraphenol compounds represented by the following formula (I):

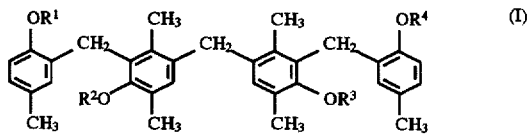

wherein $R^1$, $R^2$, $R^3$ and $R^4$ each independently represent hydrogen, 1,2-naphthoquinonediazide-4-sulfonyl or 1,2-naphthoquinonediazide-5-sulfonyl. Said 1,2-naphthoquinonediazide-4-sulfonyl or 1,2-naphthoquinonediazide-5-sulfonyl can be represented by the following formulae, respectively:

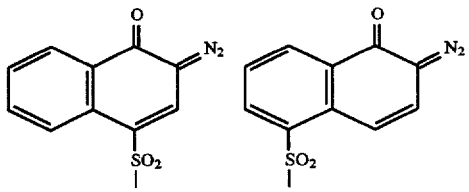

The present invention also provides a process for producing a compound of the formula (I) wherein R1, R2, R3 and R4 are all hydrogen, namely 4,4'-methylenebis[2-(2-hydroxy-5-methylbenzyl)-3,6-dimethylphenol], which comprises reacting 4,4'-methylenebis(2-hydroxymethyl-3,6-dimethylphenol) with p-cresol. Further, the invention also provides a process for producing a compound of the formula (I) wherein at least one of $R^1$, $R^2$, $R^3$ and $R^4$ is 1,2-naphthoquinonediazide-4-sulfonyl or 1,2-naphthoquinonediazide-5-sulfonyl which comprises reacting 4,4'-methylenebis[2-(2-hydroxy-5-methylbenzyl)-3,6-dimethylphenol] with a 1,2-naphthoquinone-diazide-4-sulfonyl halide or 1,2-naphthoquinone-diazide-5-sulfonyl halide, respectively.

The present invention further provides a photosensitizer comprising, as an active component, a compound represented by the formula (I) wherein at least one of $R^1$, $R^2$, $R^3$ and $R^4$ is 1,2-naphthoquinonediazide-4-sulfonyl or 1,2-naphthoquinonediazide-5-sulfonyl. The present invention still further provides a photosensitive resin composition which comprises the above-mentioned photosensitizer and an alkali-soluble novolak resin.

Compounds of the formula (I) wherein at least one of $R^1$, $R^2$, $R^3$ and $R^4$ is 1,2-naphthoquinonediazide-4-sulfonyl or 1,2-naphthoquinonediazide-5-sulfonyl are useful as photosensitizers which are sensitive to radiations such as ultraviolet rays or far ultraviolet rays including excimer laser. The compound of formula (I) wherein $R^1$, $R^2$, $R^3$ and $R^4$ are all hydrogen is useful as a starting material for producing the photosensitizer.

The compound of formula (I) wherein $R^1$, $R^2$, $R^3$ and $R^4$ are all hydrogen, namely 4,4'-methylenebis[2-(2-hydroxy-5-methylbenzyl)-3,6-dimethylphenol], can be prepared, for example, by reacting 4,4'-methylenebis(2-hydroxymethyl-3,6-dimethylphenol) with p-cresol. The starting material in this reaction, i.e. 4,4'-methylenebis(2-hydroxymethyl-3,6-dimethylphenol), can be prepared, for example, by a condensation reaction of 2,5-xylenol with formaldehyde in the presence of an alkaline catalyst.

In the reaction of 4,4'-methylenebis(2-hydroxymethyl-3,6-dimethylphenol) with p-cresol, p-cresol is used in an amount generally of 5–50 moles, preferably of 8–30 moles and more preferably of 10–25 moles per 1 mole of 4,4'-methylenebis(2-hydroxy-methyl-3,6-dimethylphenol). It is preferred that an acid catalyst is present in this reaction. The acid catalyst may be either an inorganic acid such as hydrochloric acid and sulfuric acid or an organic acid such as formic acid, acetic acid, propionic acid and paratoluene sulfonic acid. Among them, a mineral acid such as hydrochloric acid and sulfuric acid, particularly hydrochloric acid, is preferred. The acid catalyst is used in an amount usually of 1 equivalent or less and preferably within a range of 0.1–0.5 equivalent based on 4,4'-methylenebis(2-hydroxymethyl-3,6-dimethylphenol).

The reaction is preferably carried out in a solvent. Aromatic solvents, particularly aromatic hydrocarbon solvents are preferred as the reaction solvent. Examples of the aromatic hydrocarbon solvents include benzene, toluene and xylene, among which toluene is preferred. The reaction solvent is used in an amount generally within a range of 0.25- to 5-fold weight, preferably 0.25- to 2-fold weight, more preferably 0.25- to 0.5-fold weight based on the total amount of 4,4'-methylenebis(2-hydroxymethyl-3,6-dimethylphenol) and p-cresol.

The reaction is carried out at a temperature usually within a range of 30°–80° C., preferably within a range of 40°–60° C., for about 2–3 hours. The reaction is usually carried out under the atmospheric pressure.

4,4'-Methylenebis[2-(2-hydroxy-5-methylbenzyl)-3,6-dimethylphenol] crystallizes as the reaction proceeds when the reaction is carried out around room temperature. When the reaction is carried out at a higher temperature, the product crystallizes upon cooling to room temperature after completion of the reaction. A crude product can be obtained by isolating the crystals and may be subjected to an optional purification step. For example, since the compound has a lower solubility in an aromatic solvent at ordinary temperature, it can be purified by crystallization from an aromatic solvent or by repetition thereof as desired. The crystallizing solvent may be the same as or different from that used in the reaction.

When this compound is used for producing a photosensitizer after forming a quinonediazide sulfonic acid ester, it is preferred to decrease its metal content by dissolving the crude product in a solvent having a solubility of 9 g/100 g or less in water, then washing with water and separating the product form water. "Solubility of 9 g/100 g or less" means that the maximum amount soluble in 100 g of water at 20° C. is 9 g or less. Further, it is preferred that 4,4'-methylenebis [2-(2-hydroxy-5-methylbenzyl)-3,6-dimethylphenol] has a solubility of 1 g/100 g or more in the solvent used here. Examples of the solvent include acetic acid esters such as ethyl acetate, n-butyl acetate and isoamyl acetate and ketones such as methyl isobutyl ketone and 2-heptanone, among which ethyl acetate is preferred.

After decreasing the metal content, an aromatic solvent may be added to the solution of 4,4'-methylenebis[2-(2-hydroxy-5-methylbenzyl)-3,6-dimethylphenol] to crystallize the desired product. The solvent used here may be the same as or different from that used in the reaction and is preferably toluene.

4,4'-Methylenebis[2-(2-hydroxy-5-methylbenzyl)-3,6-dimethylphenol] thus obtained can be converted into, for example, a quinonediazide sulfonic acid ester which may be used as a photosensitizer. In the esterification, various kinds of sulfonic acid esters having a 1,2-quinonediazide structure can be used and, among them, a 1,2-naphthoquinonediazide-4-sulfonyl halide or 1,2-naphthoquinonediazide-5-sulfonyl halide is preferred. The halogen in the sulfonyl halide may be, for example, chlorine and bromine, among which chlorine is preferred. Accordingly, 1,2-naphthoquinonediazide-4-sulfonyl chloride and 1,2-naphthoquinonediazide-5-sulfonyl chloride is preferred as an esterifying agent. Also, a mixture of 1,2-naphthoquinonediazide-4-sulfonyl halide and 1,2-naphthoquinonediazide-5-sulfonyl halide may be used.

In the esterification reaction, 1,2-naphthoquinonediazide-4-sulfonyl halide and/or 1,2-naphthoquinonediazide-5-sulfonyl halide is used in an amount usually of 1.2–4 hold, preferably of 1.4–2.5 hold, based on 4,4'-methylene-bis[2-(2-hydroxy-5-methylbenzyl)-3,6-dimethylphenol].

The reaction is usually carried out in the presence of a dehydrohalogenating agent. The dehydrohalogenating agent is generally a basic compound. Examples of the basic compound include inorganic bases such as sodium carbonate and sodium hydrogen carbonate, and amines such as ethylamine, ethanolamine, diethylamine, diethanolamine, triethylamine, N,N-dimethylaniline and N,N-diethylaniline. The dehydrohalogenating agent is used in a molar excess ratio usually of 1.05–1.5, preferably of 1.05–1.2 and more preferably of 1.1–1.2, based on 1,2-naphthoquinonediazide-4-sulfonyl halide or 1,2-naphthoquinonediazide-5-sulfonyl halide.

The esterification reaction is usually carried out in a solvent. The solvent for the reaction includes, for example, ethers, lactones and aliphatic ketones, and is preferably selected from dioxolane, 1,4-dioxane, tetrahydrofuran, γ-butyrolactone, acetone and 2-heptanone. These can be used alone or in combination of two or more. Among them, 1,4-dioxane is preferred. The solvent for reaction is used in an amount usually within a range of 2- to 6-fold weight, preferably 3- to 5-fold weight and more preferably 4- to 5-fold weight based on the total amount of 4,4'-methylenebis [2-(2-hydroxy-5-methylbenzyl)-3,6-dimethyl-phenol] and quinonediazide sulfonyl halide.

The esterification reaction well proceeds under atomospheric pressure and around room temperature but generally carried out at a temperature of 20°–30° C. for 2–10 hours.

After completion of the reaction, the desired ester crystallizes when the reaction is neutralized with an acid such as acetic acid. Then the solid substance is filtered off and the filtrate is mixed with a diluted aqueous acid solution, for example, an aqueous acetic acid solution of a about 1% by weight. The ester can be isolated by filtration, washing with water and drying.

By the esterification reaction, generally, a mixture of two or more kinds of compounds of the formula (I), namely those selected from monoester wherein any one of $R^1$, $R^2$, $R^3$ and $R^4$ is converted into quinonediazide sulfonyl, diester wherein any two are converted into quinonediazide sulfonyl, triester wherein any three are converted into quinonediazide sulfonyl and tetraester wherein all four are converted into quinonediazide sulfonyl, is produced. This mixture can usually be used as it is for a photosensitizer.

The esterified compounds can advantageously be used for photosensitizers sensitive to radiations such as ultraviolet rays and far ultraviolet rays including excimer lasers. The photosensitizer exhibits superior effects when used in a photosensitive resin composition for positive resist, combined with a novolak resin.

The alkali-soluble novolak resins usable in a photosensitive resin composition are not limited in their kind and may be any one usable in the field of resists. They can be obtained by condensing a compound having at least one phenolic hydroxyl group, namely a phenol compound, with an aldehyde in the presence of an acid catalyst. The phenol compounds as the starting material for the novolak resins include, for example, m-cresol, p-cresol, o-cresol, 2,5-xylenol, 3,5-xylenol, 3,4-xylenol, 2,3,5-trimethylphenol and 3-methyl-6-t-butylphenol. Examples of the aldehydes as the other starting material for the novolak resins include formaldehyde, acetaldehyde, benzaldehyde, glyoxal and salicylaldehyde. Particularly, formaldehyde is industrially mass-produced in the form of a 37% aqueous solution and is suitable for use. As the acid catalyst, for example, an organic acid, an inorganic acid or a salt of bivalent metal may be used. Specific examples of the acid catalyst include oxalic acid, acetic acid, paratoluene sulfonic acid, hydrochloric acid, sulfuric acid, phosphoric acid and zinc acetate. The phenol compound and the aldehyde, as the starting material, and the acid catalyst can be used singly or a combonation of two or more of each. The condensation reaction can be conducted according to conventional methods, for example, at a temperature within a range of 60°–120° C. for about 2–30 hours. The reaction may be carried out without diluent or in a suitable solvent.

The novolak resin thus obtained is preferably treated, for example by fractionation, to form a novolak resin which has a ratio of an area in a pattern of gel-permeation chromatography (GPC) for a portion having a molecular weight of 900 or less as converted into styrene being 25% or less based on the total area in the pattern except an area in the pattern for unreacted phenol compound in order to, for example, minimize undeveloped residue of the resist. Further, it is more preferred to adjust the ratio of area for the portion having a molecular weight of 900 or less as converted into styrene to 20% or less.

For example, the fractionation can be carried out according to a method in which the novolak resin is dissolved in a good solvent, for example, an alcohol such as methanol and ethanol, a ketone such as acetone, methyl ethyl ketone, and methyl isobutyl ketone, an ethylene glycol ether such as ethyl cellosolve, as ethylene glycol ether ester such as ethyl cellosolve acetate or a cyclic ether such as tetrahydrofuran and then the solution is poured into water to precipitate high molecular weight components, or a method in which the above solution is mixed with a poor solvent such as pentane, hexane and heptane, followed by phase separation.

It is also effective to add an alkali-soluble phenol compound having a molecular weight of 900 or less to the novolak resin which is enriched in high molecular weight components by the fractionation treatment. The alkali-soluble phenol compounds having a molecular weight of 900 or less preferably have two or more phenolic hydroxyl groups in the molecular structure. Examples of the alkali-soluble phenol compounds include those described in JP-A-2-275955 (corr. to EP-A-358,871). The Examples of alkali-soluble phenol compounds described in JP-A-2-275955 include:

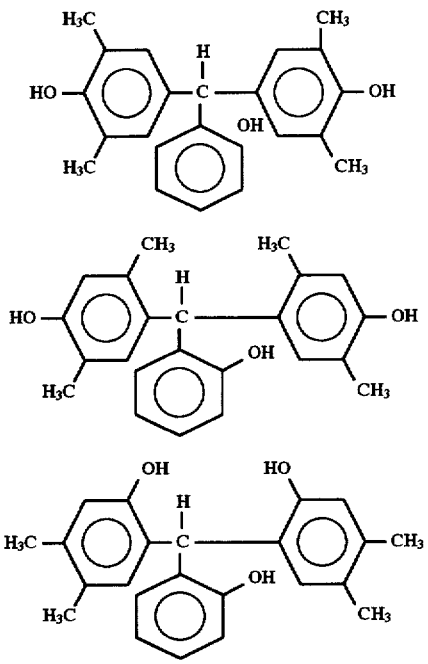

Alkali-soluble phenol compounds having a molecular weight of 900 or less are preferably used in an amount within a range of 3–40% by weight based on the total solid amount in the photosensitive resin composition.

The photosensitive resin composition containing, as photosensitizer, a compound of the formula (I) wherein at least one of $R^1$, $R^2$, $R^3$ and $R^4$ is converted into 1,2-naphthoquinonediazide-4-sulfonyl or 2-naphthoquinonediazide-5-sulfonyl may further contain another 1,2-quinonediazide sulfonic acid ester of a phenol compound. Examples of the another quinone-diazide sulfonic acid esters include those described in JP-A-5-204148, JP-A-5-323597 (corr. to EP-A-570884) or JP-A-6-167805 (corr. to EP-A-573,056). The examples of quinone-diazide sulfonic acid esters described in JP-A-204148, JP-A-5-323597 and JP-A-6-167805 include: quinone-diazide sulfonic acid esters of 2,3,4-trihydroxy benzophenone, 2,4,4-trihydroxy benzophenone, 2,3,4,4'-tetrahydroxy benzophenone, 2,3,5,5'-tetrahydroxy benzophenone,

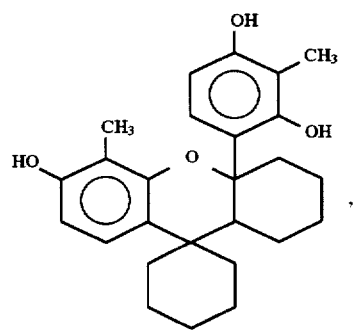
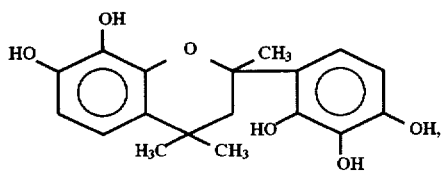
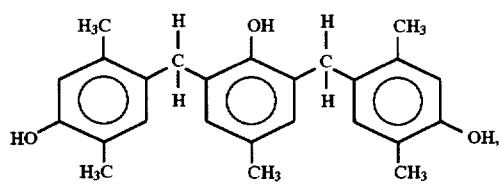
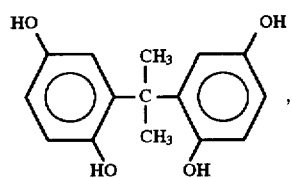
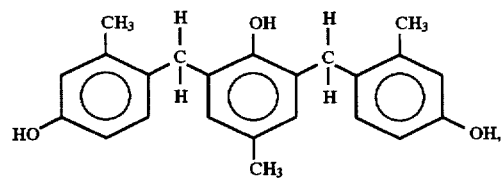
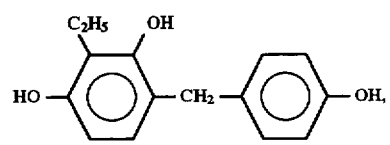
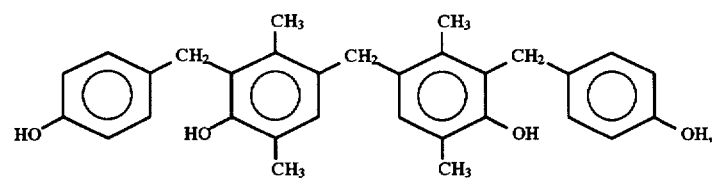
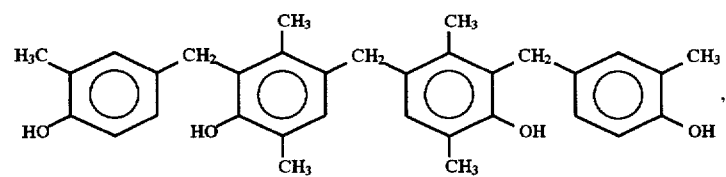

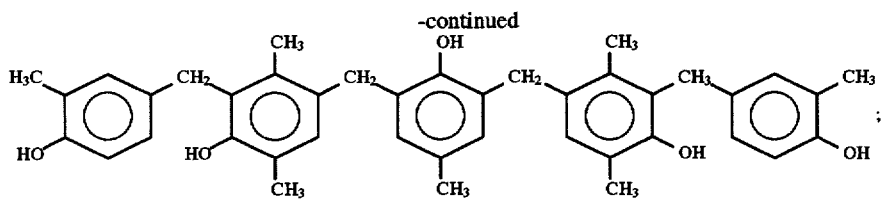

and

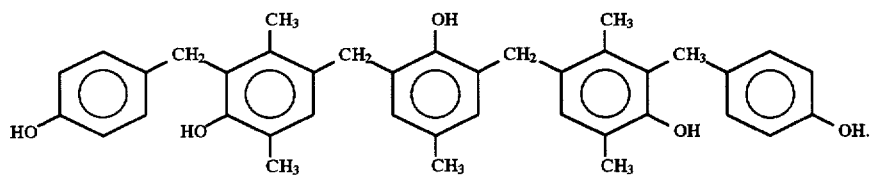

In the photosensitive resin composition of the present invention, the photosensitizer, including quinonediazide sulfonic acid esters other than a compound of the formula (I) is preferably used in an amount within a range of 10–50% by weight based on the total solid amount in the photosensitive resin composition.

Preparation of a resist solution containing photosensitive resin composition is carried out by mixing and dissolving a photosensitizer, a novolak resin and further, if necessary, an alkali-soluble phenol compound having a molecular weight of 900 or less in a solvent. As the solvent, one which has a suitable drying rate and which gives a uniform membrane after evaporation is preferred. Examples of such solvents include glycol esters such as propylene glycol monomethyl ether acetate, ethyl cellosolve acetate and methyl cellosolve acetate, esters such as ethyl pyruvate, n-amyl acetate and ethyl acetate, ketones such as 2-heptanone, cyclic esters such as γ-butyrolactone, those described in JP-A-2-220056, those described in JP-A-4-362645 and those described in JP-A-4-367863. The examples of solvents described in JP-A-2-220056, JP-A-4-362645 and JP-A-4-367863 include: propyleneglycol monomethylether acetate, propyleneglycol monoethylether acetate, γ-butyrolactone, ethyl lactate, butyl lactate, and 2-heptanone. The solvents mentioned above can be used alone or in combination of two or more.

The obtained resist solution or photosensitive resin composition may further contain a small amount of resin or dye if required.

The present invention will be described in more detail with Examples which should not be construed to limit the scope of the present invention. In the Examples, % and parts used for showing contained or added amount are weight based unless otherwise specified.

SYNTHESIS EXAMPLE 1

Production of 4,4'-methylenebis[2-(2-hydroxy-5-methylbenzyl)-3,6-dimethylphenol

Into a 500 ml three-necked flask were charged 144.16 g of p-cresol, 81.57 g of toluene and 0.43 g of 36% hydrochloric acid. Further, keeping the temperature at 50° C., 18.98 g of 4,4'-methylenebis(2-hydroxymethyl-3,6-dimethylphenol) was added in portions thereto over 1 hour. The mixture thus obtained was stirred at the same temperature for 3 hours. After cooling, the mixture was filtered and the obtained filtration mass was dissolved in 269 g of ethyl acetate. The solution was washed with 47 g of distilled water and the washing was repeated four more times. The ethyl acetate layer was concentrated and thereto 107.5 g of toluene was then added to precipitate a crystaline product. Precipitated crystals were filtered, washed with 44.54 g of toluene and the toluene washing was repeated once more. The obtained wet cake was dried a whole day and night under a reduced pressure at 60° C. to obtain 13.45 g of 4,4'-methylenebis[2-(2-hydroxy-5-methylbenzyl)-3,6-dimethylphenol].

Mass spectrum: MS 496

1H-NMR (dimethylsulfoxide) δ (ppm):

1.92 (s, 6H); 2.02 (s, 6H); 2.09 (s, 6H); 3.68 (s, 2H); 3.88 (s, 4H); 6.33 (s, 2H); 6.48 (s, 2H); 6.70 (m, 4H); 7.94 (brs, 2H); 9.22 (brs, 2H).

SYNTHESIS EXAMPLE 2

Formation of quinonediazide sulfonic acid ester

Into a 5 liter four-necked flask were charged 372.53 g of 4,4'-methylenebis[2-(2-hydroxy-5-methylbenzyl)-3,6-dimethyl-phenol], 403.02 g (2 molar excess) of 1,2-naphthoquinonediazide-5-sulfonyl chloride and 3877.73 g of dioxane and they were completely dissolved. Then, 182.142 g of triethylamine was added dropwise at 20°–30° C. over 1 hour. After completion of the addition, the mixture was stirred at 30° C. for 3 hours. Thereafter, 45.04 g of acetic acid was added and the mixture was stirred for 1 hour at the same temperature. The reaction mixture was filtered and the residue was washed with 403.02 g of dioxane. The combined filtrate and washing were poured into a mixture of 171 g of acetic acid and 17123 g of deionized water and stirred for 1 hour. The precipitated crystals were filtered and the filter cake was washed by stirring in 3891 g of deionized water. This washing was repeated further three times, followed by a filtration. The obtained filter cake was dried at 40° C. to obtain 747 g of the ester (referred to as Photosensitizer A).

1H-NMR (dimethylsulfoxide) δ (ppm):

1.75 (s, 6H); 2.06 (s, 6H); 2.06 (s, 6H); 3.65 (s, 2H); 3.86 (s, 4H); 6.39 (s, 2H); 6.48 (s, 2H); 6.63 (d, 8.2 Hz, 2H); 6.89 (d, 8.2 Hz, 2H); 7.42 (d, 10 Hz, 2H); 7.66 (dd, 8.8 Hz, 2H); 7.75 (d, 10 Hz, 2H); 8.02 (s, 2H); 8.24 (d, 8 Hz, 2H); 8.60 (d, 8 Hz, 2H).

REFERENCE EXAMPLE

Production of novolak resin

Into a 1000 ml four-necked flask were charged 148.5 g of m-cresol, 121.5 g of p-cresol, 252 g of methyl isobutyl ketone, 37.0 g of 10% oxalic acid and 84.8 g of 90% aqueous acetic acid. While heating the mixture in an oil bath at 100°

C. with stirring, 129.5 g of 37% formalin was added dropwise thereto over 40 minutes and reaction was carried out for further 15 hours. Then, the mixture was washed with water and dried to obtain 466 g of a methyl isobutyl ketone solution containing 42.3% novolak resin. The resin had a weight average molecular weight, converted into styrene, of 4300 as measured by GPC.

Into a 5 l separable flask having a drain cock at the bottom, was charged 450 g of the solution obained above. Further, 909.6 g of methyl isobutyl ketone and 996.1 g of n-heptane were added thereto. After stirring at 60° C. for 30 minutes, the mixture was left to stand and subjected to phase-separation. To the lower layer mass obtained by the separation, was added 380 g of 2-heptanone. Thereafter, methyl isobutyl ketone and n-heptane were removed therefrom by evaporation to give a 2-heptanone solution of a novolak resin. The resin had a weight average molecular weight, converted into styrene, of 9000 as measured by GPC, and a ratio of an area for a portion having a molecular weight of 900 or less as converted into polystyrene was 14% based on the total area in the pattern.

APPLICATION EXAMPLES 1–3

15 parts, converted into solid weight, of a solution of the novolak resin in 2-heptanone obtained in the Reference Example, 3.9 parts of 4,4'-(2-hydroxybenzylidene)di-2,6-xylenol as an additive, an amount of a 1,2-naphthoquinonediazide photosensitizer shown in Table 1 and 2-heptanone were mixed in such manner that the total amount of 2-heptanone in the solution became 50 parts and they were dissolved. The solution was filtered through a fluorine resin filter having a pore size of 0.2 µm to obtain a resist solution.

The above resist solution was coated onto silicone wafers washed according to conventional manner, using a spin coater to 1.1 µm thickness. Then, the wafers were baked on a hot plate at 90° C. for 1 minute. Thereafter, they were exposed to irradiation with a reduced projection exposing machine (=stepper; manufactured by Nikon, NSR 1755i 7A, NA=0.5) having an exposing wave length of 365 nm (i-ray) changing the exposure amount in steps. Then, the wafers were baked on a hot plate at 110° C. for 1 minute and developed with a developing solution "SOPD" (manufactured by Sumitomo Chemical Company, Limited) for 1 minute to give a positive patterns. Each of the positive patterns were evaluated in the following manner. The results are shown in Table 1.

EFFECTIVE SENSITIVITY

This is expressed in terms of the exposure amount at which the 0.50 µm line and space pattern become 1:1.

RESOLUTION

The size of the line and space pattern separable without loss of film thickness is measured with a scanning electron microscope at an exposure amount at which the line and space pattern become 1:1 (effective sensitivity).

PROFILE

The shape of cross-section of 0.45 µm line and space pattern at the effective sensitivity was observed with a scanning electron microscope.

FOCUS (DEPTH OF FOCUS)

The width of focus when 0.40 µm line and space pattern was separable without loss of film thickness at the effective sensitivity was measured with a scanning electron microscope.

SCUM

Presence or absence of scum (undeveloped residue) was observed with a scanning electron microscope.

γ-VALUE

The ascent of a line obtained by plotting normalized thickness of membrane (=residual thickness of membrane/ original thickness of membrane) with respect to the exposure amount was measured and tan δ was taken as the γ-value.

TABLE 1

| Application Example No. | 1 | 2 | 3 |
|---|---|---|---|
| Composition | | | |
| Photosensitizer | A 5 parts B 1 part | A 7 parts | A 8 parts |
| Properties | | | |
| Effective Sensitivity | 300 msec | 330 msec | 380 msec |
| Resolution | 0.32 µm | 0.31 µm | 0.30 µm |
| Profile | | | |
| Depth of Focus | 1.5 µm | 1.5 µm | 1.5 µm |
| Scum | Not observed | Not observed | Not observed |
| γ-value | 7.62 | 8.77 | 10.1 |

PHOTOSENSITIZER A

The ester obtained in Synthesis Example 2

PHOTOSENSITIZER B A condensate of 4-(4-hydroxy-2,5-dimethylbenzyl)pyrogallol and 1,2-naphthoquinone-diazide-5-sulfonyl chloride in a molar ration of 1:1.

The tetraphenol compounds of the present invention represented by formula (I) wherein at least one of $R^1$, $R^2$, $R^3$ and $R^4$ represents 1,2-naphthoquinonediazide sulfonyl are useful as a photosensitizer for a photosensitive resin composition and the compound wherein $R^1$, $R^2$, $R^3$ and $R^4$ are all hydrogen is useful as a precursor of such photosensitizer. The photosensitive resin compositions comprising said photosensitizer which is converted into a 1,2-naphthoquinonediazide sulfonic acid ester is well balanced among various properties as the resist for minute processing of semiconductors such as high sensitivity, high resolution (γ-value), high heat resistance, good profile, good focus allowance and little development residue.

We claim:

1. A tetraphenol compound represented by the formula (I):

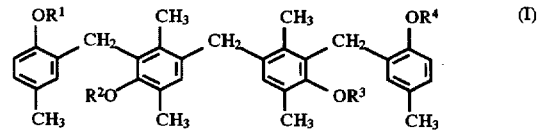

wherein $R^1$, $R^2$, R3 and $R^4$ represent, independently of one another, hydrogen, 1,2-naphthoquinonediazide-4-sulfonyl or 1,2-naphthoquinonediazide-5-sulfonyl.

2. A compound according to claim 1, in which $R^1$, $R^2$, $R^3$ and $R^4$ are all hydrogen.

3. A compound according to claim 1, in which at least one of $R^1$, $R^2$, $R^3$ and $R^4$ is 1,2-naphthoquinonediazide-4-sulfonyl or 1,2-naphthoquinonediazide-5-sulfonyl.

4. A process for producing a compound of claim 1 which comprises reacting 4,4'-methylenebis(2-hydroxymethyl-3,6-dimethylphenol) with p-cresol.

5. A process for producing a compound of claim 3 which comprises reacting 4,4'-methylenebis[2-(2-hydroxy-5-methylbenzyl)-3,6-dimethylphenol] with a 1,2-naphthoquinonediazide-4-sulfonyl halide or 1,2-naphthoquinonediazide-5-sulfonyl halide.

6. A photosensitizer comprising a tetraphenol compound represented by the formula (I):

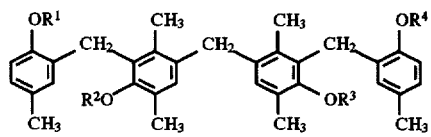

(I)

wherein one of $R^1$, $R^2$, $R^3$ and $R^4$ represents 1,2-naphthoquinonediazide-4-sulfonyl or 1,2-naphthoquinonediazide-5-sulfonyl and the remainder represent, independently of one another, hydrogen, 1,2-naphthoquinonediazide-4-sulfonyl or 1,2-naphthoquinonediazide-5-sulfonyl.

7. A photosensitive resin composition comprising an alkali-soluble novolak resin and a photosensitizer of claim 6.

8. A composition according to claim 7, in which the alkali-soluble novolak resin is a condensate of a phenol compound with an aldehyde, a ratio of an area in a pattern of gel-permeation chromatography for a portion thereof, having a molecular weight of 900 or less converted into styrene, being 25% or less based on the total area in the pattern except an area in the pattern for unreacted phenol compound.

* * * * *